United States Patent [19]

Beatty

[11] Patent Number: 4,887,607
[45] Date of Patent: Dec. 19, 1989

[54] APPARATUS FOR AND METHOD OF SPECTRAL ANALYSIS ENHANCEMENT OF POLYGRAPH EXAMINATIONS

[76] Inventor: Robert F. Beatty, 7927 Marquand Ave., West Hills, Calif. 91304

[21] Appl. No.: 169,224

[22] Filed: Mar. 16, 1988

[51] Int. Cl.$^4$ .............................................. A61B 5/02
[52] U.S. Cl. .................................... 128/670; 128/668
[58] Field of Search ............... 128/670, 671, 697, 693, 128/688, 716, 709

[56] References Cited

U.S. PATENT DOCUMENTS 2,235,894  3/1941  Lee ...................................... 128/688
2,538,125  11/1945 Reid ...................................... 127/688

FOREIGN PATENT DOCUMENTS 908746  8/1964  Canada ............................... 128/688

Primary Examiner—Max Hindenburg
Assistant Examiner—Scott M. Getzow
Attorney, Agent, or Firm—Harry B. Field

[57] ABSTRACT

An apparatus for and method of improving polygraph testing comprises parallel processing of output response signals of a human being by a polygraph machine and a spectral analyzer and then comparing and contrasting the output results for more qualified interpretations.

4 Claims, 6 Drawing Sheets

APPARATUS FOR AND METHOD OF SPECTRAL ANALYSIS ENHANCEMENT OF POLYGRAPH EXAMINATIONS

BACKGROUND OF THE INVENTION

1. Field of the Invention

This invention relates to polygraph machines and more specifically to the enhancement of the polygraph data evaluation by the incorporation of a spectral analyses thereby eliminating inconclusive results and producing supplemental and recognizable polygraph data for more accurate examinations.

2. Discussion of the Prior Art

A conventional polygraph machine or lie detector as described in the Article "The Polygraph", by Burke M. Smith, Scientific American, January 1967, Vol. 216, No. 1, pg 25 in use today helps to determine whether or not a person is telling the truth. The apparatus is designed to detect and record changes that occur in the human body as an individual responds to certain questions. Such changes are known to occur in the respiratory system, pulse, blood pressure, nervous system, and sweat gland response.

Although many experts believe that such tests are extremely accurate measures of a person's integrity and veracity, the polygraph apparatus and the results are continuously being challenged and may fail to provide conclusive results.

In the current polygraph data reduction process, the data is only monitored from a time history standpoint using an uncalibrated amplitude scale as an integrity indicator with relative amplitudes compared to known true and false statement. True response generate little pen motion and false statements cause large pen motions, or pegging. In scaling to minimize the pegging, "deceptive" or "somewhat false" responses may cause the pens to oscillate only slightly. This may be a result of the frequency response of the polygraph machine being too low (machines of this type typically cannot record above 60 Hz), or indicative of possibly another response frequency present other than a fundamental. It, of course must be realized that most system response has some oscillation to it but the frequency content can greatly vary.

It is well known that viewing data in only time history terms may be insufficient in providing conclusive structural integrity evidence. When problems occur other frequencies are typically produced which can be interpreted as signs of deterioration and a means of early detection provided. This appears to be the case in monitoring a human being's integrity. For example, the feeling one has that from the way a person makes a statement an impression he is lying in his tone of voice is given. The monitors used on a polygraph test may detect a tenseness, or modulation, in the involuntary nervous system which causes not only a tone change to be heard, but also may be detectable in the normally monitored polygraph data.

OBJECTS OF THE INVENTIONS

Therefore, it is an object of the present invention to improve the reliability of present polygraph examinations.

A further object of the present invention is to provide improved polygraph apparatus.

Another object of the present invention is to enhance the ability of polygraph operators to obtain accurate, incontrovertible data.

Yet another object of the present invention is to eliminate background scatter in polygraph results.

Still a further object of the present invention is to enable polygraph operators to maintain current test operating procedures and monitoring systems.

Other objects, advantages and novel features of the present invention will become apparent from the following detailed description of the invention when considered in conjunction with the accompanying drawing.

SUMMARY OF THE INVENTION

In accordance with the present invention there is provided the apparatus for and method of enhancing the accuracy of polygraph examinations with supplemental data. The apparatus comprises a polygraph machine having input leads running from the human body to the polygraph machine so that the involuntary human responses to questions can be monitored and a spectrum analyzer electronically connected in parallel with the polygraph machine such that the involuntary human output responses are concurrently received with the input to the polygraph machine and are processed to eliminate undesirable pen oscillations and false background data in the frequency domain for comparative purposes.

DETAILED DESCRIPTION OF THE PREFERRED EMBODIMENTS

Figure 1:
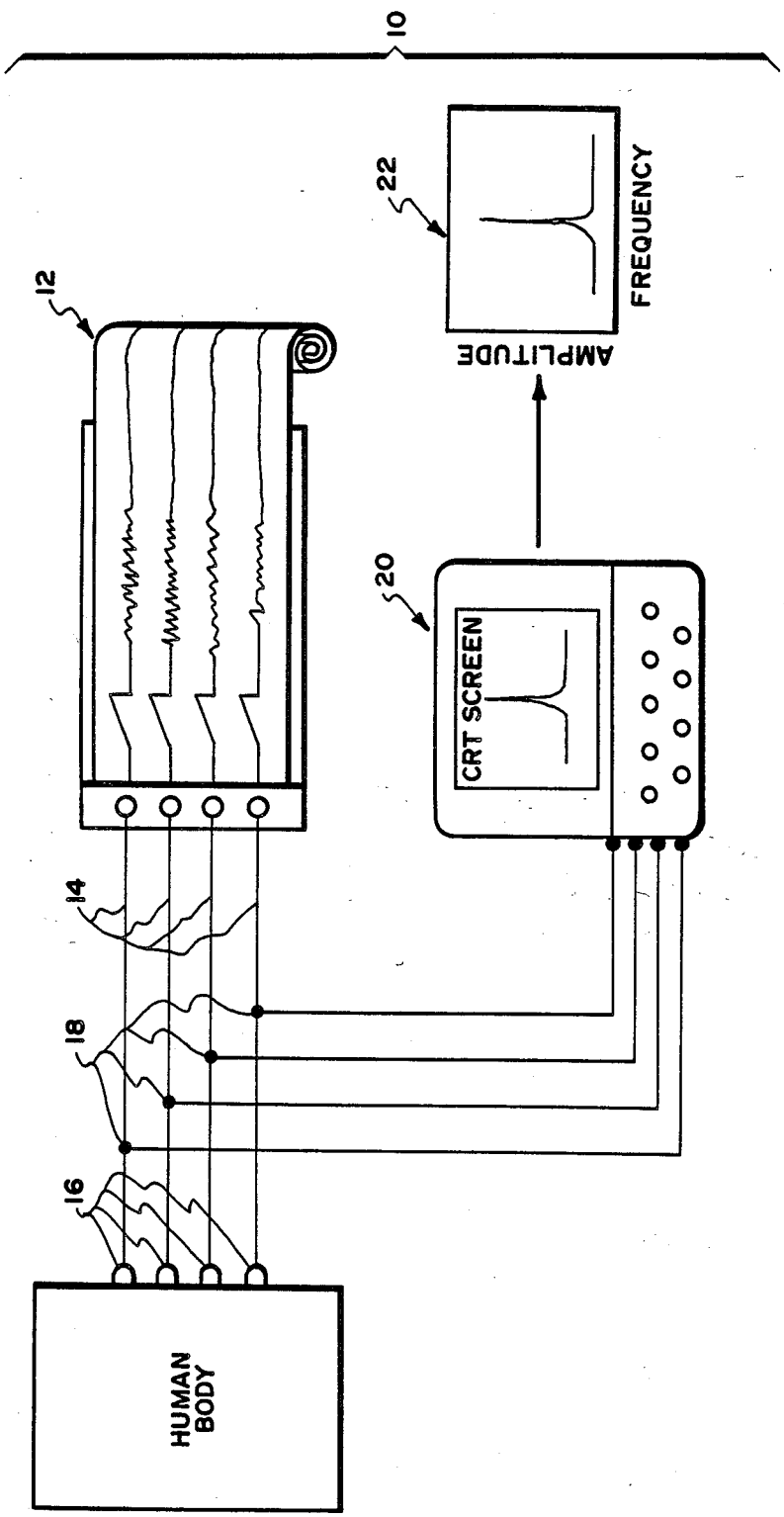
FIG. 1 is a schematic representation of the present invention incorporating a polygraph machine and a spectrum analyzer.

In accordance with the present invention depicted in FIG. 1, there is provided an improved polygraph apparatus generally designated 10. Polygraph apparatus 10 comprises a polygraph machine generally designated 12 including a set of input leads 14, and means for connecting 16 input leads to the human body. To this basic polygraph machine there is added an electrical signal splitting means 18 for transferring identical outputs to a first and a second component. The first component is directed to polygraph machine 12 while the second component is concurrently directed in parallel to a spectrum analyzer generally designated 20. A typical spectrum analyzer 20 and its operation are described in detail in "The Fundamentals of Signal Analysis Application Note 243," By Hewlett-Packard, July 1982. As an added feature, the spectral analysis results can either be stored in the analyzer's memory or output to a plotter 22 where outputs from both the spectral analyzer and polygraph machine could be compared and contrasted so decisions can be based on both interpretations.

In operation, the frequency response of the polygraph machine 12 should be extended to twice the frequency range of the human voice, approximately 1000 Hz as a minimum. This can be accomplished by parallel processing of the data such that in addition to using the existing method the monitored data can be split into the aforementioned spectrum analyzer 20 for processing time requiring only about a tenth of a second. The frequency data can be calibrated while the amplitude time histories are being calibrated by defining spectra of truthful and false responses, and then determining if harmonic frequencies occur in the false response. If so, later testimony of similar spectral content can be judged a lie. This may not be the case in only time history processing where additional non-fundamental frequencies may not cause significant pen deflection due to machine filtering of the high frequency data content. Most standard spectral analysis machine can also store data for retrieval. Additional processing of this acquired response can be performed by dividing by either a stored true or false spectrum. Whichever results in a coherence (logical connection) value of approximately unity can be considered the proper assessment. This is technically called a transfer function and may be an accurate measure of the truth.

Although spectral analysis has never hitherto been applied to polygraph testing and the monitoring of the human body, certain sophisticated industries have applied this type of technology to monitoring hardware. Thus, it is expected that an explanation of another application of this type of technology and of the necessary comparative analysis will help in the understanding of this new polygraph system and data analysis method.

Figure 2:
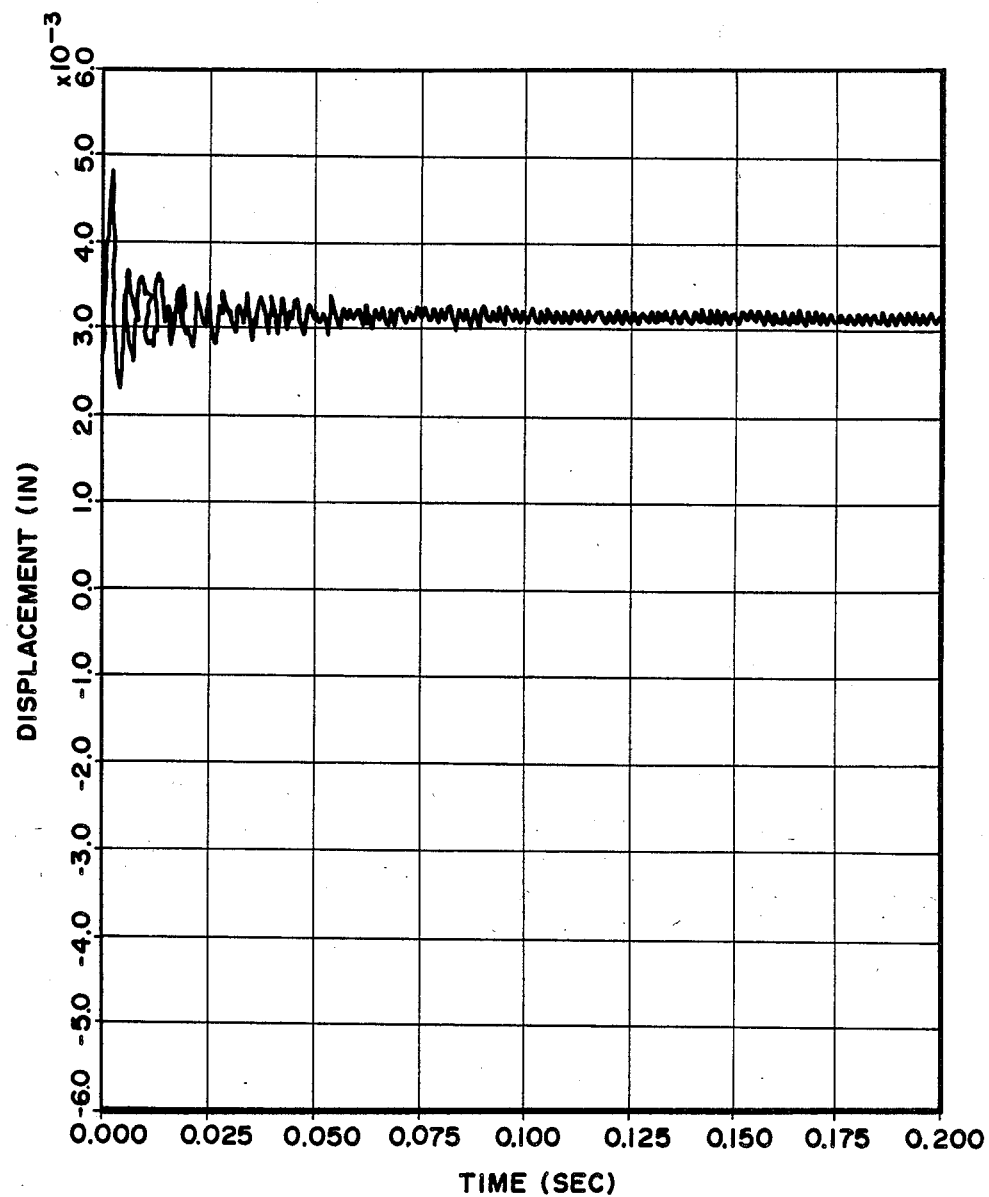
FIG. 2 is a graphical representation of typical time history data.
Figure 3:
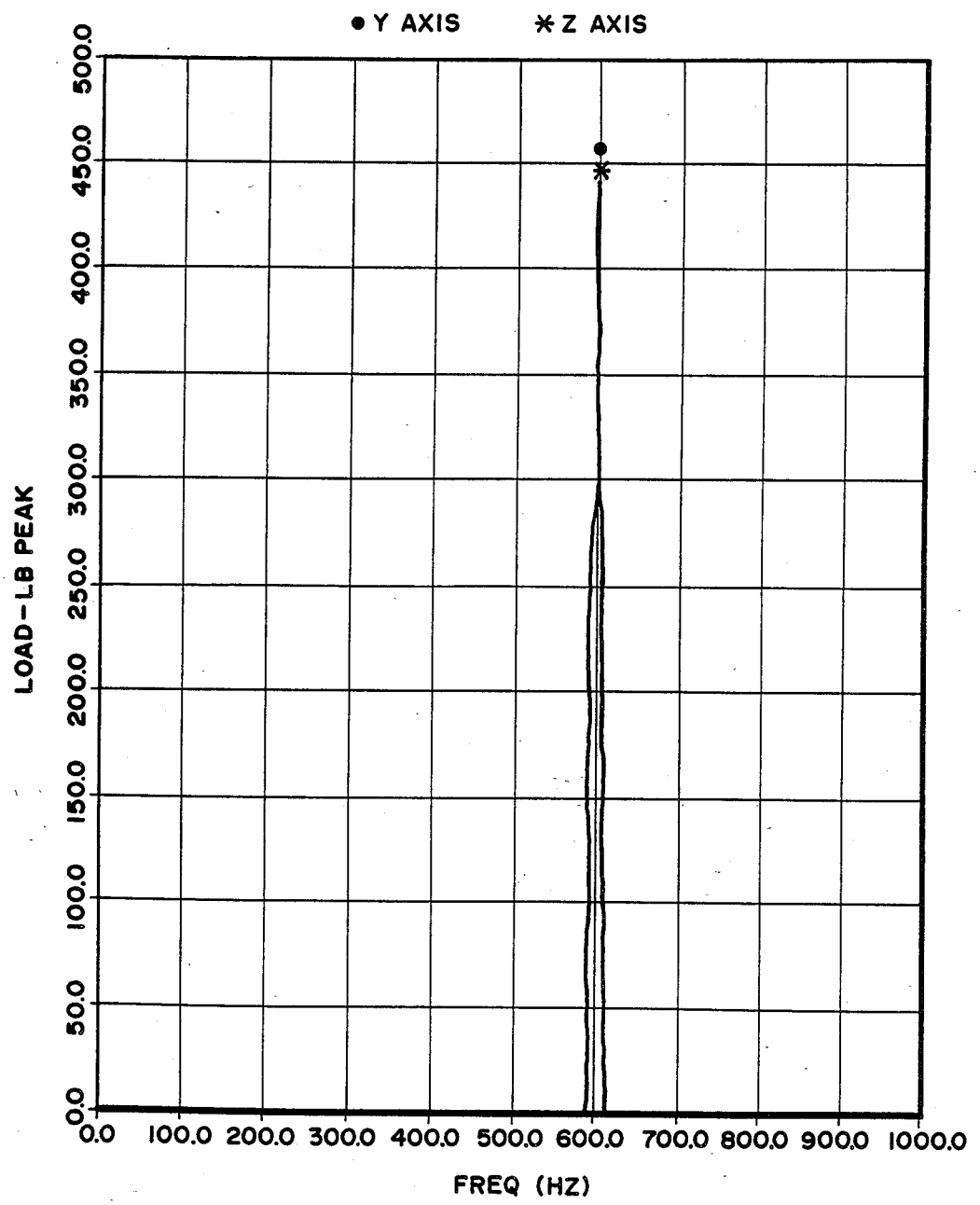
FIG. 3 is a graphical representation of typical fundamental frequency spectral data.
Figure 4:
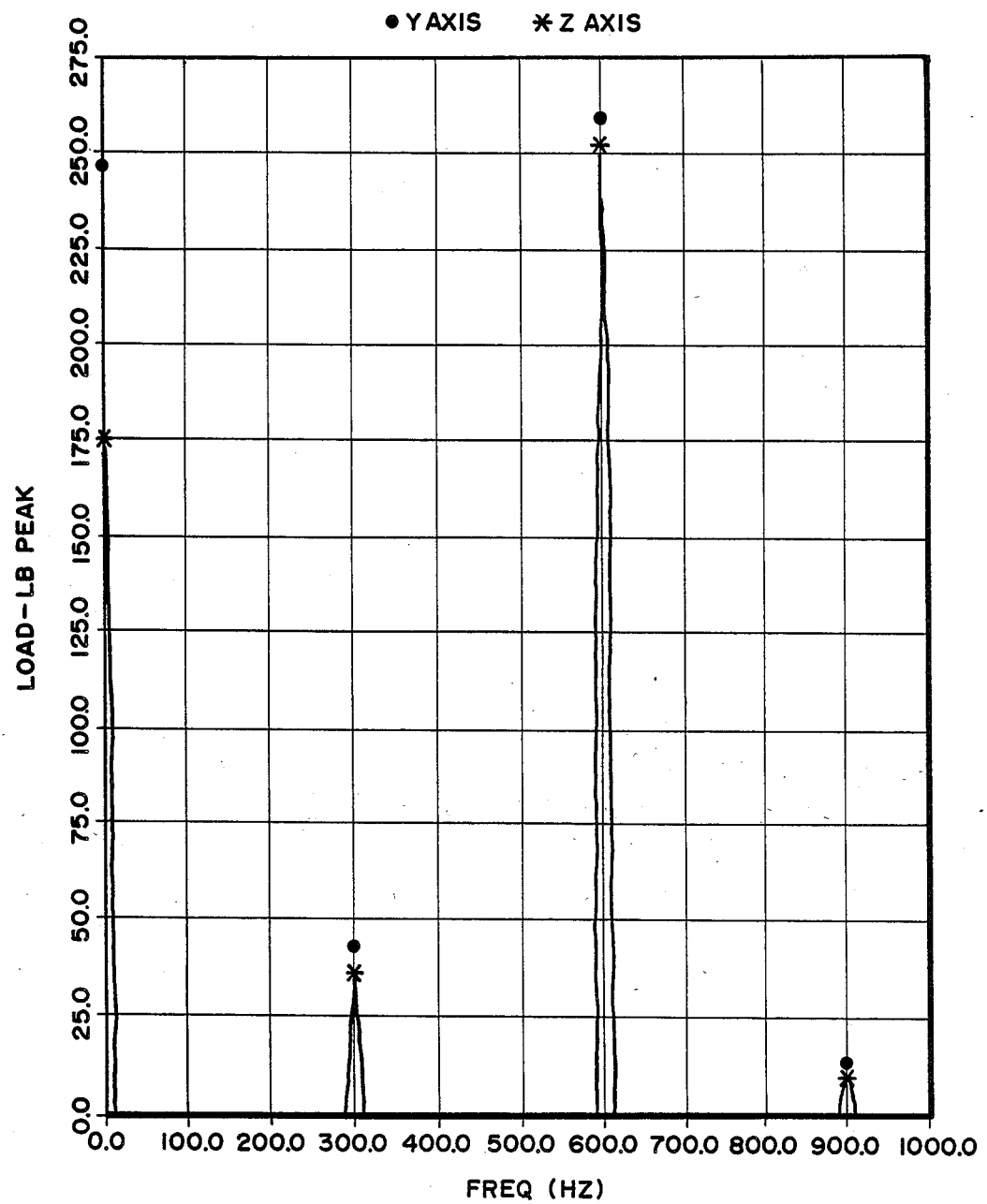
FIG. 4 is a graphical representation of typical spectral data with harmonic frequency content.
Figure 5:
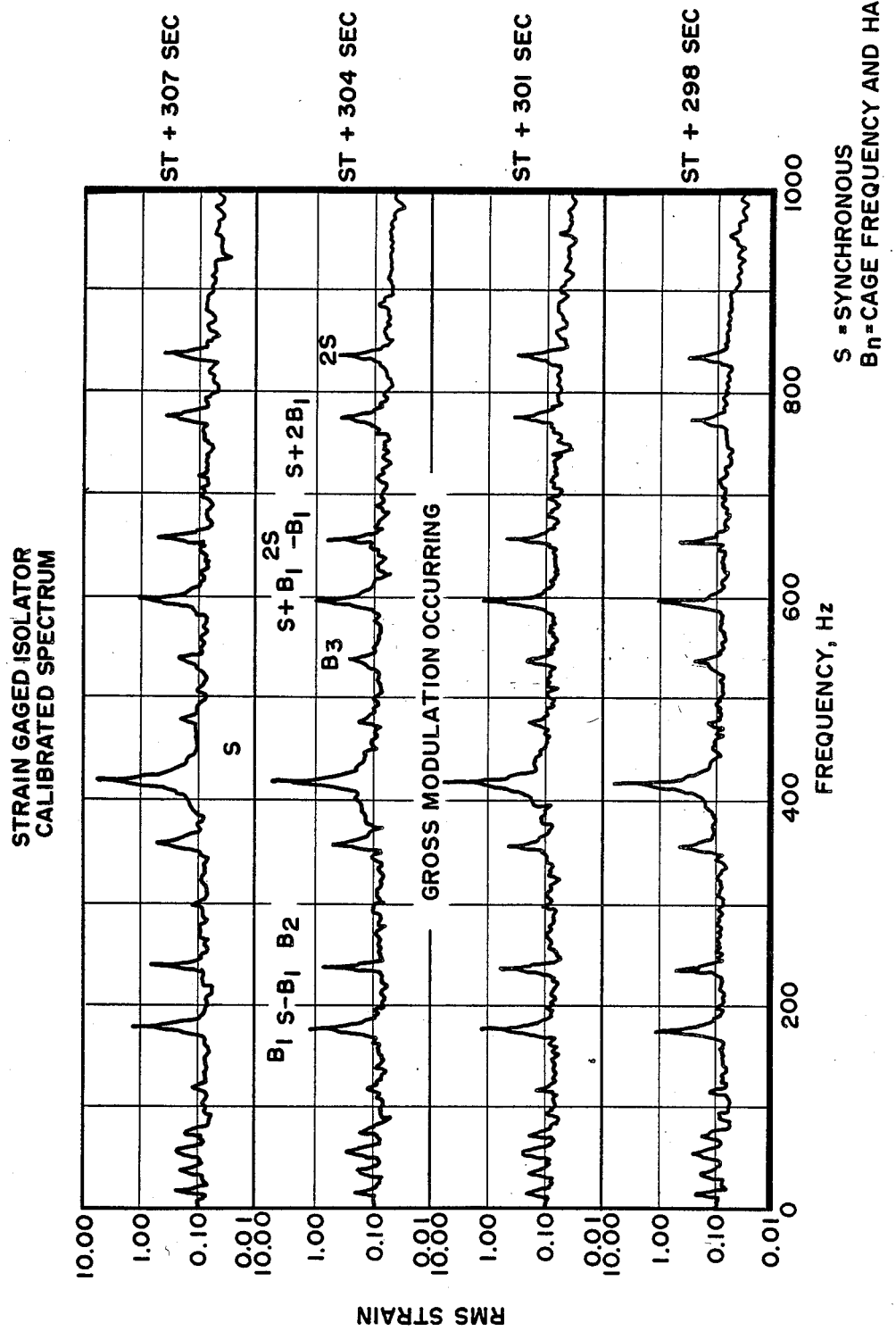
FIG. 5 is a graphical representation of typical spectral data for continuous monitoring.
Figure 6:
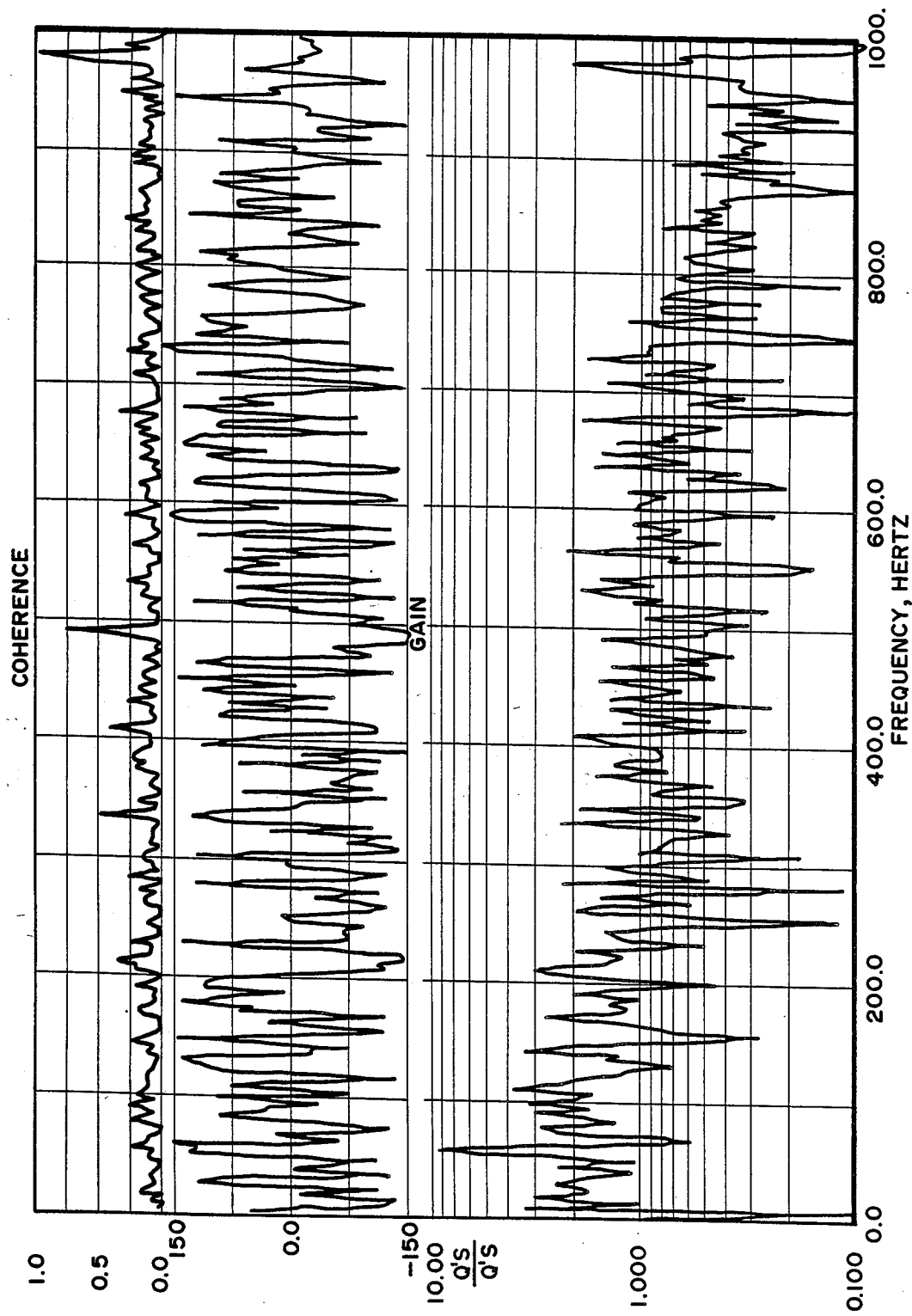
FIG. 6 is a graphical representation of typical transfer function data showing gain, phase, and coherence.

Turning now to FIG. 2 there is shown a time history example, somewhat similar to polygraph data response from a single sensor. The drawback to this type of data processing occurs when more than one frequency is present. This response can have a dominant frequency amplitude with harmonics or the resultant time history may also be significantly altered if filtered. Normally a spectral analysis is required to separate these data with multiple harmonic frequencies. Spectral analysis transforms data from the time domain to the frequency domain and plots the processed data as amplitude versus frequency. FIG. 3 is an example of a spectral analysis of time history data which has a fundamental frequency. When a system degrades, harmonic frequencies are typically produced as shown in FIG. 4. In this case a subharmonic frequency was produced. Such may be the case with the uncontrolled portion of the human nervous system and false statement could produce similar harmonic frequencies for evaluation by the examiner indicative of loss of integrity. These spectra can also be stacked one after another as the evaluations are performed in real time as shown in the presentation of FIG. 5. These evaluations can be expanded to include transfer functions of current response divided by stored truthful response data where the calculated amplitude, ratio and coherence relationship, or logical connection, can be used to assess integrity. On the coherence calculation, a greater than about 0.8 value at the fundamental and harmonic frequencies is considered good correlation. A statement is judged based on good correlation relative to prior truthful or false responses. Typical transfer function data is shown in FIG. 6.

Obviously, many modifications and variations of the present invention are possible in light of the above teachings. It is therefore to be understood that, within the scope of the appended claims, the invention may be practiced otherwise than as specifically described.

What is claimed and desired to be secured by Letters Patent of the United States is:

1. A polygraph examination apparatus comprising in combination:

a polygraph machine including input leads adapted to be connected to the human body so that the specific human body functions of galvanic skin response, blood pressure, respiration, and pulse and their associated output signals can be monitored; and a spectrum analyzer electronically connected in parallel with said polygraph machine such that the output signals of the human body functions being monitored on said polygraph machine are concurrently monitored on said spectrum analyzer.

2. The polygraph examination apparatus of claim 1 wherein the output of said spectrum analyzer are output to means for generating functional output plots.

3. The polygraph examination apparatus of claim 1 wherein said spectrum analyzer further comprises an access memory for storing said spectrum analyzer output.

4. A method of analyzing polygraph data which comprises:

splitting the signal output such as galvanic skin response, blood pressure, respiration and pulse, obtained from a human body so that a first portion of the identical said output goes to a polygraph machine and a second portion of the said output signal is conveyed in parallel to a spectrum analyzer;

recording said first portion of said output signal on a polygraph machine;

processing said second portion of said output signal through said spectrum analyzer;

outputting said spectrum analyzer results; and comparing and contrasting said polygraph machine recordings with said spectrum analyzer results to make interpretations and decisions based on both outputs.

* * * * *